(12) United States Patent
Van Der Heide et al.

(10) Patent No.: US 10,647,647 B2
(45) Date of Patent: May 12, 2020

(54) PROCESS FOR THE PREPARATION OF GLYCOLS

(71) Applicant: SHELL OIL COMPANY, Houston, TX (US)

(72) Inventors: Evert Van Der Heide, Amsterdam (NL); Pieter Huizenga, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/466,826

(22) PCT Filed: Dec. 4, 2017

(86) PCT No.: PCT/EP2017/081349
§ 371 (c)(1),
(2) Date: Jun. 5, 2019

(87) PCT Pub. No.: WO2018/104216
PCT Pub. Date: Jun. 14, 2018

(65) Prior Publication Data
US 2019/0345084 A1    Nov. 14, 2019

(30) Foreign Application Priority Data
Dec. 7, 2016 (EP) .................................. 16202641

(51) Int. Cl.
| | | |
|---|---|---|
| *C07C 29/132* | (2006.01) | |
| *C07C 29/60* | (2006.01) | |
| *B01J 19/00* | (2006.01) | |
| *B01J 23/30* | (2006.01) | |
| *B01J 23/755* | (2006.01) | |
| *C07C 31/20* | (2006.01) | |
| *C07C 31/26* | (2006.01) | |
| *B01J 23/745* | (2006.01) | |
| *B01J 23/75* | (2006.01) | |

(52) U.S. Cl.
CPC ......... *C07C 29/132* (2013.01); *B01J 19/0046* (2013.01); *B01J 23/30* (2013.01); *B01J 23/755* (2013.01); *C07C 29/60* (2013.01); *C07C 31/20* (2013.01); *C07C 31/202* (2013.01); *C07C 31/205* (2013.01); *C07C 31/26* (2013.01); *B01J 23/745* (2013.01); *B01J 23/75* (2013.01); *B01J 2219/0059* (2013.01)

(58) Field of Classification Search
CPC ....... C07C 29/60; C07C 29/132; C07C 31/20; C07C 31/202; C07C 31/205; C07C 31/26; B01J 19/0046; B01J 2219/0059; B01J 23/30; B01J 23/75; B01J 23/745; B01J 23/755
See application file for complete search history.

(56) References Cited

U.S. PATENT DOCUMENTS 6,291,725 B1    9/2001    Chopade et al.

FOREIGN PATENT DOCUMENTS

| WO | WO 2015/028398 A1 * | 3/2015 | ............. C07C 29/00 |
|---|---|---|---|
| WO | 2016114661 A1 | 7/2016 | |
| WO | 2018022538 A1 | 2/2018 | |

OTHER PUBLICATIONS

International Search Report and Written Opinion received for PCT Patent Application No. PCT/EP2017/081349 dated Jan. 30, 2018, 8 pages.
Ji et al., "Direct Catalytic Conversion of Cellulose into Ethylene Glycol Using Nickel-Promoted Tungsten Carbide Catalysts", Angewandte Chemie Int. Ed., vol. 47, Issue No. 44, Oct. 20, 2008, pp. 8510-8513.

* cited by examiner

*Primary Examiner* — Yate' K Cutliff

(57) ABSTRACT

The invention provides a process for the preparation of ethylene glycol and 1,2-propylene glycol from starting material comprising one or more saccharide, wherein the process comprises the steps of: i) providing the starting material and hydrogen to a first reactor and reacting said starting material and hydrogen therein in the presence of a solvent and a first catalyst system comprising a retro-aldol catalyst composition and a hydrogenation catalyst composition; ii) continuously removing a first reactor product stream from the first reactor, said first reactor product stream comprising ethylene glycol, 1,2-propylene glycol and in the range of from 2 to 40 wt % of sugar alcohols; iii) contacting said first reactor product stream in a second reactor in the presence of hydrogen with a second catalyst system comprising at least a hydrogenation catalyst composition; and iv) converting a portion of the sugar alcohols in the second reactor into ethylene glycol and/or 1,2-propylene glycol to provide a second reactor product stream comprising ethylene glycol, 1,2-propylene glycol and in the range of from 10 to 80% of the amount of sugar alcohols present in the first reactor product stream.

8 Claims, No Drawings

PROCESS FOR THE PREPARATION OF GLYCOLS

CROSS REFERENCE TO RELATED APPLICATIONS

This is a national stage application of International Application No. PCT/EP2017/081349, filed 4 Dec. 2017, which claims benefit of priority to European Patent Application No. 16202641.3, filed 7 Dec. 2016.

FIELD OF THE INVENTION

The present invention relates to a process for the preparation of ethylene and propylene glycols from saccharide-containing feedstock.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focussed on producing chemicals, including glycols, from renewable feedstocks, such as sugar-based materials. The conversion of sugars to glycols can be seen as an efficient use of the starting materials with the oxygen atoms remaining intact in the desired product.

Current methods for the conversion of saccharides to glycols revolve around a hydrogenation/hydrogenolysis process as described in Angew. Chem. Int. Ed. 2008, 47, 8510-8513.

As with many chemical processes, the reaction product stream in these processes comprises a number of desired materials as well as diluents, by-products and other undesirable materials. During the hydrogenolysis of glucose and glucose-containing molecules, to form MEG and MPG, some of the glucose is hydrogenated to sorbitol and other sugar alcohols. Such sugar alcohols cannot undergo retro-aldol conversion to form MEG and MPG in the hydrogenolysis reaction. As a result, sorbitol and other sugar alcohols are side products and decrease the overall yield of the higher valued MEG and MPG.

In order to provide a high value process, the desirable product or products must be obtainable from the reaction product stream in high purity with a high percentage recovery of each product and with as low as possible use of energy, chemical components and complex equipment.

Sugar alcohols will generally be separated from the desired products as a heavies stream in one or more distillation steps. In certain processes, such heavies may be used as a convenient recycle solvent stream for a homogeneous hydrogenolysis catalyst. Thus, the presence of a certain amount of sugar alcohols in the reaction system is desirable. However, with more sugar alcohols being made during each reaction cycle, an undesirable build up can occur and removal of the sugar alcohols, e.g. via a bleed, is required.

Application U.S. application Ser. No. 62/367,384 describes a process for the conversion of sorbitol into ethylene glycol and propylene glycol by contacting a sorbitol feed with hydrogen in a reactor in the presence of a solvent and a bi-functional catalyst system. The sorbitol feed may be derived from a process for the conversion of saccharide-containing feedstock to MPG and MEG.

It would be desirable to provide a process that includes converting a portion of the sugar alcohols present in the product stream of a process for the conversion of saccharide-containing feedstock to MPG and MEG in-situ and in the presence of MEG and MPG, while retaining sufficient sugar alcohols in the product stream to allow efficient recycle of homogeneous catalyst materials.

SUMMARY OF THE INVENTION

Accordingly, the present invention provides a process for the preparation of ethylene glycol and 1,2-propylene glycol from starting material comprising one or more saccharide, wherein the process comprises the steps of:
i) providing the starting material and hydrogen to a first reactor and reacting said starting material and hydrogen therein in the presence of a solvent and a first catalyst system comprising a retro-aldol catalyst composition and a hydrogenation catalyst composition;
ii) continuously removing a first reactor product stream from the first reactor, said first reactor product stream comprising ethylene glycol, 1,2-propylene glycol and in the range of from 2 to 40 wt % of sugar alcohols;
iii) contacting said first reactor product stream in a second reactor in the presence of hydrogen with a second catalyst system comprising at least a hydrogenation catalyst composition; and
iv) converting a portion of the sugar alcohols in the second reactor into ethylene glycol and/or 1,2-propylene glycol to provide a second reactor product stream comprising ethylene glycol, 1,2-propylene glycol and in the range of from 10 to 80% of the amount of sugar alcohols present in the first reactor product stream.

DETAILED DESCRIPTION OF THE INVENTION

The present inventors have surprisingly found that the sugar alcohols, including sorbitol, present in the reactor product stream containing sugar alcohols, MEG and MPG in a solvent may be partially converted to MEG and/or MPG without decomposition of the MEG and MPG already present. Said conversion may also occur in the presence of hydrogenolysis catalyst compositions comprising tungstates. Said tungstates are generally present in such reaction product streams from a reactor in which starting material comprising one or more saccharide is converted into glycols including MEG and MPG.

The starting material for the subject process comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof.

If the starting material comprises oligosaccharides or polysaccharides, it is preferable that it is subjected to pre-treatment before being fed to the reactor in a form that can be converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment. However, after said pre-treatment, the starting material still comprises mainly monomeric and/or oligomeric saccharides. Said saccharides are, preferably, soluble in the reaction solvent.

Preferably, the starting material supplied to the first reactor after any pre-treatment comprises saccharides selected from starch and/or hydrolysed starch. Hydrolysed starch comprises glucose, maltose and oligomeric forms of glucose. Said saccharide is suitably present as a solution, a suspension or a slurry in the solvent.

The starting material and hydrogen are reacted in the presence of a solvent. The solvent may be water or a $C_1$ to $C_6$ alcohol or polyalcohol (including sugar alcohols) or mixtures thereof. Preferred $C_1$ to $C_6$ alcohols include methanol, ethanol, 1-propanol and iso-propanol. Polyalcohols of use include glycols, particularly products of the hydrogenation/retro-aldol reaction, glycerol, erythritol, threitol, sorbitol and mixtures thereof. Preferably, the solvent comprises water.

The first catalyst system used in the first reactor preferably comprises two components. The first component is a heterogeneous hydrogenation catalyst composition.

Both the hydrogenation catalyst composition in the first catalyst system and the hydrogenation catalyst composition in the second catalyst system preferably comprise one or more materials selected from transition metals from groups 8, 9 or 10 or compounds thereof, with catalytic hydrogenation capabilities.

More preferably, the hydrogenation catalyst compositions comprise one or more metals selected from the list consisting of iron, cobalt, nickel, ruthenium, rhodium, palladium, iridium and platinum. This metal or metals may be present in elemental form or as compounds. It is also suitable that this component is present in chemical combination with one or more other ingredients in the hydrogenation catalyst composition. It is required that the hydrogenation catalyst compositions have catalytic hydrogenation capabilities and are capable of catalysing the hydrogenation of material present in the reactors.

In the process of the invention, the second hydrogenation catalyst composition is preferably heterogeneous with respect to the reaction mixture and is optionally supported within the reactor to create a fixed bed.

In one embodiment, one or both of the heterogeneous hydrogenation catalyst compositions comprise metals supported on a solid support. In this embodiment, the solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Alternatively, one or both of the heterogeneous hydrogenation catalyst compositions may be present as Raney material, such as Raney nickel, preferably present in a pelletised form.

The heterogeneous hydrogenation catalyst compositions are individually preferably present in fixed beds. Said fixed beds may also contain inert material in order to ensure a suitable ratio of catalyst composition to feed. Said inert material may comprise, for example, glass spheres or support materials that have not been impregnated with metals. Suitably, the particle size of the inert materials is comparable with that of the catalyst composition.

In another embodiment, the metal may be present unsupported in catalyst beds within the reactor. In this embodiment inert material may also be present within the reactor in order to ensure a suitable ratio of catalyst composition to feed.

The heterogeneous hydrogenation catalyst compositions are suitably preloaded into the reactors before the reaction is started.

The second component of the catalyst system is a retro-aldol catalyst composition. Said retro-aldol catalyst composition preferably comprises one or more compound, complex or elemental material comprising tungsten, molybdenum, vanadium, niobium, chromium, titanium or zirconium. More preferably the retro-aldol catalyst composition comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the retro-aldol catalyst composition comprises one or more compound, complex or elemental material selected from those containing tungsten or molybdenum.

The retro-aldol catalyst composition may be present as a heterogeneous or a homogeneous catalyst composition. In one embodiment, the retro-aldol catalyst composition is heterogeneous and is supported in the reactor along with the heterogeneous hydrogenation catalyst composition. In this embodiment, the retro-aldol catalyst composition may be supported on the same support or a different support to the hydrogenation catalyst composition. In another embodiment, the retro-aldol catalyst composition is homogeneous with respect to the reaction mixture.

Depending on the physical state of the retro-aldol catalyst composition and any components contained therein, they may be preloaded into the reactors or, if they are in liquid form or present as a solution or slurry in a solvent, they may be fed into the reactor as required in a continuous or discontinuous manner during the process of the present invention.

It will be readily understood that, although the retro-aldol catalyst composition may be provided to the first reactor in one chemical form, it may be present in the first and second reactors and the first and second reactor product stream in one or more different chemical forms.

The weight ratio of the retro-aldol catalyst composition (based on the amount of metal in said composition) to sugar feed is suitably in the range of from 1:1 to 1:1000. The weight ratio of the hydrogenation catalyst composition (based on the amount of metal in said composition) to sugar feed is suitably in the range of from 10:1 to 1:100.

The weight ratio of the retro-aldol catalyst composition to the hydrogenation catalyst composition (based on the amount of metal in each composition) is typically in the range of from 1:1000 to 1:1.

The process of the present invention takes place in the presence of hydrogen. Preferably, the process of the present reaction takes place in the absence of air or oxygen. In order to achieve this, it is preferable that the atmosphere in the reactor be evacuated and replaced with an inert gas (e.g. nitrogen or argon) and then hydrogen repeatedly, after loading of any initial reactor contents, before the reaction starts.

The temperature in the first reactor is at least 160° C., preferably at least 170° C., most preferably at least 190° C. The temperature in the first reactor is at most 270° C., preferably at most 250° C.

The pressure in the first reactor is at least 1 MPa, preferably at least 2 MPa, most preferably at least 3 MPa. The pressure in the first reactor is preferably at most 25 MPa, more preferably at most 20 MPa, most preferably at most 18 MPa.

The WHSV in the first reactor is suitably in the range of from 0.1 to 1000 g(liquid feed)/g(catalyst)/hour.

A first reactor product stream is continuously removed from the first reactor. Said first reactor product stream comprises ethylene glycol, 1,2-propylene glycol and in the range of from 2 to 40 wt % of sugar alcohols.

The first reactor product stream comprise at least 2 wt %, preferably at least 5 wt % of sugar alcohols. The first reactor product stream comprise at most 40 wt %, preferably at most 30 wt %, more preferably at most 20 wt % of sugar alcohols.

Sugar alcohols present in the first reactor stream include, but are not limited to glycerol, erythritol, threitol and sorbitol.

The first reactor product stream comprises, as glycols, at least MEG and MPG. These, and other, glycols are typically present at a concentration in the range of from 1 to 40 wt % of the overall stream.

In the first reactor product stream, MEG is suitably present as at least 10 wt %, preferably as at least 30 wt % of the non-solvent fraction of the stream. MEG is suitably present as at most 95 wt %, preferably as at most 90 wt %, most preferably as at most 80 wt % of the non-solvent fraction of the stream.

In such a reaction product stream, MPG is suitably present as at least 2 wt %, preferably as at least 4 wt % of the non-solvent fraction of the stream. MPG is suitably present as at most 45 wt %, preferably as at most 20 wt % of the non-solvent fraction of the stream.

1,2-butanediol (1,2-BDO) may also be present in the stream as a desirable product.

As well as the glycols and sugar alcohols, the first reactor product stream may comprise solvent (particularly water), oxygenates, hydrocarbons, catalyst, degradation products, and gases in any composition. The variety of compounds and their concentration depend on the saccharide-containing feedstock and the various hydrogenation and retro-aldol conversion conditions, including catalysts, reaction conditions such as temperature, pressure and saccharide concentration. However, suitably the retro-aldol reactions have gone to completion and the first reactor product stream contains less than 5 wt %, preferably less than 2 wt %, more preferably less than 1 wt %, even more preferably less than 0.5 wt %, most preferably substantially no saccharides when considered as a weight percentage of the overall stream.

When the retro-aldol catalyst composition is present in homogeneous form, said retro-aldol catalyst composition will also be present in the first reactor stream.

As used herein, the term 'glycol' has its standard definition, that it a diol in which the two hydroxyl groups are on vicinal carbon atoms. The terms ethylene glycol, MEG and monoethylene glycol are used interchangeably to refer to monoethylene glycol (chemical formula $H_2C(OH)$—$C(OH)H_2$). The terms propylene glycol, MPG and monopropylene glycol are used interchangeably to refer to monopropylene glycol (chemical formula $H_3CCH(OH)$—$C(OH)H_2$).

The first reactor product stream is contacted with hydrogen in a second reactor in the presence of a second catalyst system comprising at least a hydrogenation catalyst composition.

The hydrogenation catalyst composition in the second catalyst system may be the same or different to the hydrogenation catalyst composition in the first catalyst system.

The conditions in the second reactor are suitable for the conversion of sugar alcohols to MEG and/or MPG. Preferably the conditions in the second reactor include one or more of a higher temperature, a lower pressure, a lower hydrogen partial pressure and a lower WHSV than the conditions in the first reactor.

The temperature in the second reactor is at least 180° C., preferably at least 200° C., most preferably at least 210° C. The temperature in the second reactor is at most 270° C., preferably at most 250° C., more preferably at most 240° C.

The pressure in the second reactor is at least 1 MPa, preferably at least 2 MPa, most preferably at least 3 MPa. The pressure in the second reactor is preferably at most 25 MPa, more preferably at most 20 MPa, most preferably at most 18 MPa.

The WHSV in the second reactor is suitably in the range of from 0.001 to 100 g(liquid feed)/g(catalyst)/hour.

A portion of the sugar alcohols in the first reactor product stream are converted in the second reactor into MEG and MPG and a second reactor product stream is removed from the second reactor. Said second reactor product stream comprises in the range of from 10 to 80% of the sugar alcohols present in the first reactor product stream.

A portion of the sugar alcohols present in the first reactor product stream are not converted in the second reactor and, therefore, remain in the second reactor product stream. This has the advantage that sugar alcohols provide an excellent solvent system for typical homogeneous retro-aldol catalyst compositions and can be used as a medium for recycling said retro-aldol catalyst composition to the first reactor after separation from the desired products by known means.

Preferably, the MEG and MPG present in the first reactor product stream are not degraded in the second reactor. Therefore, preferably the second reactor product stream contains at least 100% of the amount of MEG and at least 100% of the amount of MPG present in the first reactor product stream.

Optionally, a third, 'finishing', reactor is also used. In one embodiment this 'finishing' reactor is positioned downstream of the second reactor. In another embodiment of the invention, this 'finishing' reactor is positioned downstream of the first reactor and upstream of the second reactor. In a further embodiment of the invention there are two 'finishing' reactors, one positioned downstream of the first reactor and one positioned downstream of the second reactor.

Said finishing reactor or reactors would preferably be operated at a lower temperature than the first and second reactors. Suitably the finishing reactor(s) would be operated at a temperature in the range of from 50 to 200° C., more preferably at a temperature in the range of from 60 to 150° C., most preferably at a temperature in the range of from 70 to 120° C. Preferably said finishing reactor is a trickle bed reactor containing a hydrogenation catalyst composition. Said hydrogenation catalyst composition may be chosen from the same hydrogenation catalyst compositions as used in the first and second reactors. The finishing reactor or reactors allows the retro-aldol and hydrogenation reactions carried out in the first reactor to continue to completion.

The term 'reactor' is used herein to describe an area in which a reaction takes place. Said reactors may be part of the same reactor vessel with each reactor comprising one or more catalyst-containing beds within the overall reactor vessel.

The present invention is further illustrated in the following Examples.

EXAMPLES

Hastelloy C batch autoclaves (75 ml), with magnetic stir bars, were used to screen various conditions and catalyst systems.

Known weights of catalysts, caustic and sorbitol were added to the autoclaves along with 30 ml of the solvent (water). The loaded autoclave was then purged three times with nitrogen, followed by hydrogen purge.

The hydrogen pressure was then raised to ~14 MPa of hydrogen and the autoclave was sealed and left stirring overnight to do a leak test.

The next morning the autoclave was depressurised to the target hydrogen pressure (10.1 MPa) at room temperature, and closed. The temperature was then ramped to the target run temperature as a fast ramp.

The autoclave was held at the target temperature for known durations of time (135 min), while both the temperature and pressure were monitored. After the required run time had elapsed, the heating was stopped, and the reactor was cooled down to room temperature, depressurised, purged with nitrogen and then opened.

The contents of the autoclave were then analyzed via Gas Chromatography (GC) or High Pressure Liquid Chromatography (HPLC) after being filtered.

Table 1 provides details of the reaction conditions and results for Comparative (Comp.) Examples 1 and 2 and Examples 1 and 2 (of the invention).

TABLE 1

| Example | Comp. 1 | Comp. 2 | Example 1 | Example 2 |
|---|---|---|---|---|
| Catalyst 1 | 68% Ni/ZrO$_2$ | 68% Ni/ZrO$_2$ | 68% Ni/ZrO$_2$ | 68% Ni/ZrO$_2$ |
| Amount of Catalyst 1 (g) | 0.375 | 0.625 | 1.25 | 2.5 |
| Amount of Na$_2$CO$_3$ | 0.375 | 0.156 | — | — |
| Catalyst 2 | — | — | Na meta-tungstate | Na meta-tungstate |
| Amount of catalyst 2 (g) | — | — | 0.3 | 0.3 |
| Water (g) | 30 | 30 | 30 | 30 |
| Feed | Sorbitol | Sorbitol | Sorbitol | Sorbitol |
| Amount of feed g | 10 | 10 | 10 | 10 |
| Run temp | 220 | 220 | 220 | 220 |
| Run time (min) | 135 | 135 | 135 | 135 |
| pH after reaction | 4.87 | 4.46 | 3.84 | 4.04 |
| Sorbitol % | 30.7 | 16.8 | 31.0 | 16.8 |
| Isosorbide % | 1.7 | 1.6 | 1.2 | 0.9 |
| Xylitol % | 2.5 | 2.1 | 2.3 | 1.2 |
| Erythritol % | 1.7 | 1.5 | 1.5 | 0.8 |
| Threitol % | 1.7 | 1.7 | 2.8 | 2.1 |
| Glycerol % | 6.7 | 8.0 | 7.5 | 4.6 |
| MEG % | 6.5 | 14.3 | 13.0 | 14.4 |
| MPG % | 12.9 | 14.3 | 13.0 | 14.4 |
| 1,2-BDO % | 1.8 | 2.7 | 2.6 | 3.2 |
| Glycolic acid % | 1 | 0.6 | 0 | 0 |
| Lactic acid % | 3.5 | 1.9 | 0 | 0 |
| Formic acid % | 0 | 0 | 0 | 0 |
| Acetic acid % | 1.7 | 1.5 | 0.4 | 0.7 |
| Propionic acid % | 0 | 0 | 0.9 | 2.4 |

Catalyst 1 is a hydrogenation catalyst composition. This catalyst is capable of catalysing hydrogenation and hydrocracking reactions. Catalyst 2 is a retro-aldol catalyst composition. For usual hydrocracking of sugar alcohols, caustic material (Na$_2$CO$_3$) is added to the reaction mixture to reduce the pH of the reaction mixture and encourage cracking. Comparative examples 1 and 2 demonstrate such a process.

However, in a process to produce MEG and MPG from starting material comprising one or more saccharide, a retro-aldol catalyst composition will be present in the reaction mixture. Inventive examples 1 and 2 demonstrate that cracking can still be carried out in the presence of such retro-aldol catalyst compositions, that are generally thought to act as catalyst poisons. Indeed, these examples demonstrate that caustic is not required and the pH of the resulting product will still be suitable for the next process step.

In inventive examples 1 and 2 a decrease in WHSV (g(feed)/g(catalyst)/minute) is provided by increasing the amount of catalyst present. In a continuous process, this could also be achieved by a slower flow rate.

Inventive examples 1 and 2 also demonstrate the same increase in glycols (MEG, MPG and 1,2-BDO) yield with increasing sorbitol conversion that is shown for the comparative examples. A further advantage is seen in the reduced yields of certain acids (glycolic, lactic, acetic, formic) for these examples.

This process allows for a reduced build-up of sugar alcohols and, therefore, a reduced recycle and bleed stream requirement in the overall process.

That which is claimed is:

1. A process for the preparation of ethylene glycol and 1,2-propylene glycol from starting material comprising one or more saccharide, wherein the process comprises the steps of:
    i) providing the starting material and hydrogen to a first reactor and reacting said starting material and hydrogen therein in the presence of a solvent and a first catalyst system comprising a retro-aldol catalyst composition and a hydrogenation catalyst composition;
    ii) continuously removing a first reactor product stream from the first reactor, said first reactor product stream comprising ethylene glycol, 1,2-propylene glycol and in the range of from 2 to 40 wt % of sugar alcohols;
    iii) contacting said first reactor product stream in a second reactor in the presence of hydrogen with a second catalyst system comprising at least a hydrogenation catalyst composition; and
    iv) converting a portion of the sugar alcohols in the second reactor into ethylene glycol and/or 1,2-propylene glycol to provide a second reactor product stream comprising ethylene glycol, 1,2-propylene glycol and in the range of from 10 to 80% of the amount of sugar alcohols present in the first reactor product stream.

2. The process as claimed in claim 1, wherein the retro-aldol catalyst composition is homogeneous with respect to the reaction mixture.

3. The process as claimed in claim 1, wherein the retro-aldol catalyst composition comprises one or more compound, complex or elemental material selected from those containing tungsten.

4. The process as claimed in claim 1, wherein the first and second hydrogenation catalyst compositions each comprise one or more metals selected from the list consisting of iron, cobalt, nickel, ruthenium, rhodium, palladium, iridium and platinum.

5. The process as claimed in claim 1, wherein the first reactor product stream comprises in the range of from 5 to 30 wt % of sugar alcohols.

6. The process as claimed in claim 1, wherein the conditions in the second reactor include one or more of a higher temperature, a lower pressure, a lower hydrogen partial pressure and a lower WHSV than the conditions in the first reactor.

7. The process as claimed in claim 1, wherein the sugar alcohols remaining in the second reactor product stream are used as a medium for recycling the retro-aldol catalyst composition to the first reactor.

8. The process as claimed in claim 1, wherein a finishing reactor is used either before, after or both before and after the second reactor and wherein said finishing reactor is operated at a temperature lower than the second reactor.

* * * * *